United States Patent [19]
Kobayashi

[11] Patent Number: 5,143,077
[45] Date of Patent: Sep. 1, 1992

[54] CONSTANT-RATE DISCHARGE VALVE, AND ELECTRONIC AUTOMATIC SPHYGMOMANOMETER USING SAME

[75] Inventor: Susumu Kobayashi, Fujinomiya, Japan

[73] Assignee: Terumo Kabushiki Kaisha, Tokyo, Japan

[21] Appl. No.: 686,879

[22] Filed: Apr. 16, 1991

Related U.S. Application Data

[63] Continuation of Ser. No. 480,648, Feb. 15, 1990, abandoned.

[30] Foreign Application Priority Data

Feb. 20, 1989 [JP] Japan ................... 1-38444

[51] Int. Cl.⁵ .................................. A61B 5/02
[52] U.S. Cl. ........................ 128/677; 137/505.41; 128/680; 128/685
[58] Field of Search ............... 128/680-683, 128/685, 672, 677; 285/14; 137/505.39, 505.41

[56] References Cited

U.S. PATENT DOCUMENTS

| Re. 32,587 | 2/1988 | Matsuura et al. | 128/685 |
|---|---|---|---|
| 1,933,379 | 10/1933 | Mock | 137/505.39 |
| 2,069,808 | 2/1937 | Andersson | 137/505.41 |
| 3,363,621 | 1/1968 | Whitmore | 128/685 |
| 3,504,663 | 4/1970 | Edwards | 128/685 |
| 4,113,284 | 9/1978 | Blocker | 285/14 |
| 4,198,031 | 4/1980 | Ezekiel et al. | 128/685 |
| 4,200,259 | 4/1980 | Ueda | 128/685 |
| 4,356,827 | 11/1982 | Uemura et al. | 128/681 |
| 4,587,974 | 5/1986 | Link | 128/685 |
| 4,690,171 | 9/1987 | Johnston | 128/685 |
| 4,754,777 | 7/1988 | Frode | 137/505.39 |
| 4,841,980 | 6/1989 | Lee | 128/685 |
| 4,898,204 | 2/1990 | Wallace | 137/505.41 |
| 4,926,874 | 5/1990 | Lee | 128/685 |

FOREIGN PATENT DOCUMENTS 61-142003 9/1986 Japan.

Primary Examiner—Ruth S. Smith
Assistant Examiner—Robert L. Nasser, Jr.
Attorney, Agent, or Firm—Frishauf, Holtz, Goodman & Woodward

[57] ABSTRACT

A constant-rate discharge valve adapted so as to render a discharge rate constant includes a housing having an internal air chamber and an open hole open to the atmosphere, first and second air passageways each having one end open to the air chamber and communicating with each other via the air chamber, a control orifice provided in the second air passageway to control air flow rate, and a valve body disposed in the housing so as to partition the air chamber from the open hole. The valve body interrupts communication between the first and second air passageways when pressure in the air chamber is greater than a predetermined pressure and permits communication between the first and second air passageways when the pressure in the air chamber is less the predetermined pressure. An electronic automatic sphygmomanometer using this constant-rate discharge valve discharges air at a constant flow rate.

8 Claims, 3 Drawing Sheets

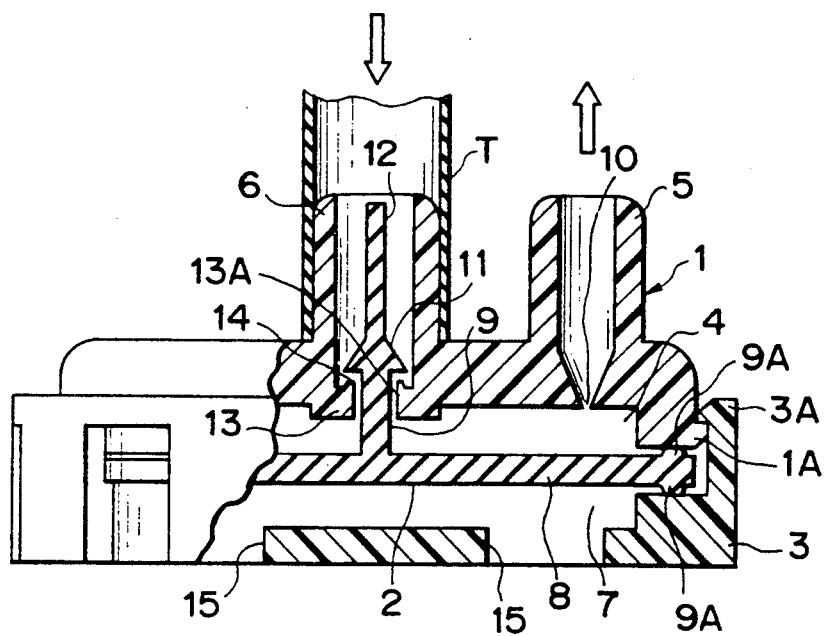
F I G. 1A
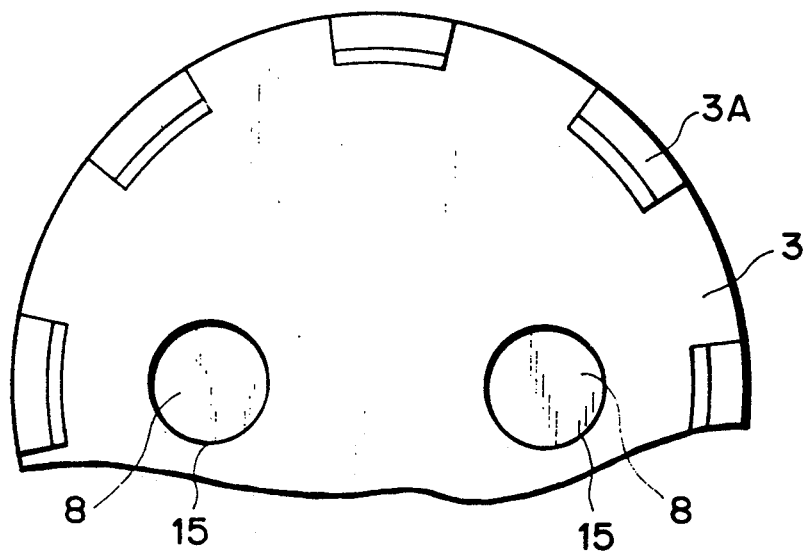
F I G. 1B

CONSTANT-RATE DISCHARGE VALVE, AND ELECTRONIC AUTOMATIC SPHYGMOMANOMETER USING SAME

This application is a continuation of application Ser. No. 480,648, filed Feb. 15, 1990.

BACKGROUND OF THE INVENTION

1. Field of the Invention

This invention relates to a constant-rate discharge valve and an electronic automatic sphygmomanometer using such a discharge valve.

2. Description of the Prior Art

Conventionally, a manual sphygmomanometer is provided with a constant-rate discharge valve. Such a valve is provided at the entrance of a rubber bulb for inflating a cuff, and the cuff is deflated at a constant rate by manually adjusting a regulating valve.

In order to measure blood pressure using such a manual sphygmomanometer, first the cuff pressure is raised to a value above systolic blood pressure, after which the cuff pressure is adjusted manually by the regulating valve to deflate the cuff at a constant rate. During this deflation, systolic and diastolic blood pressure are measured by detecting Korotkoff sounds.

In an electronic automatic sphygmomanometer, the constant-rate discharge valve cannot be manually adjusted. For this reason, the constant-rate discharge valve used is so adapted that the cuff is deflated at a constant rate.

FIG. 4A is a front view of a conventional constant-rate discharge valve, and FIG. 4B is a side view of the conventional constant-rate discharge valve. These views show a typical arrangement of a constant-rate discharge valve employed in an electronic automatic sphygmomanometer. With reference to FIGS. 4A and 4B, there is shown a constant-rate discharge valve main body 100 having one end open to the atmosphere and another end formed into a hollow cylindrical member penetrated by a small orifice 101. The valve is fitted into a pipe T indicated by the slanting lines.

As for the operation of the constant-rate valve thus constructed, air which is passed through the interior of the pipe T is discharged at a constant rate by passing through the orifice 101.

Thus, the constant-rate discharge valve of the manual sphygmomanometer involves difficulty in terms of operation, as mentioned above. Though the constant-rate discharge valve of the fully automatic sphygmomanometer constructed as described above eliminates this difficulty, it is difficult to maintain the precisely machined state of the orifice, and therefore disparities in dimensions and shape arise. As a result, it is difficult to maintain a constant discharge state without variance.

Another problem is that the amount of discharged air cannot be adjusted with the fully automatic sphygmomanometer constructed as described above.

SUMMARY OF THE INVENTION

Accordingly, an object of the present invention is to provide a constant-rate discharge valve which does not require a troublesome operation and is capable of maintaining a constant discharge state without variance, as well as a fully automatic sphygmomanometer employing this constant-rate discharge valve.

Another object of the present invention is to provide a constant-rate discharge valve in which discharge flow rate can be adjusted, as well as an electronic sphygmomanometer which employs this constant-rate discharge valve.

In order to attain the foregoing object, the present invention provides a constant-rate discharge valve adapted so as to render a discharge rate constant, comprising a housing having an internal air chamber and a hole open to the atmosphere, first and second air passageways each having one end open to the air chamber and communicating with each other via the air chamber, the second air passageway having a control orifice for controlling air flow rate, and a valve body disposed in the housing so as to partition the air chamber from the hole, the valve body interrupting communication between the first and second air passageways when pressure in the air chamber is greater than a predetermined pressure and permitting communication between the first and second air passageways when the pressure in the air chamber is less the predetermined pressure.

In a preferred embodiment of the constant-rate discharge valve, air which has flown in from the first air passageway passes through the air chamber and the control orifice and is discharged into the atmosphere from the second air passageway, at which time the valve body is actuated by a pressure difference across upstream and downstream sides of the control orifice produced by the flow rate of the entrant air, the valve body being closed by the pressure difference when the pressure difference is large and opened by the pressure difference when the pressure difference is small, whereby the flow rate of air discharged from the second air passageway is rendered constant.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1A is a partial sectional view illustrating a first embodiment of a constant-rate discharge valve according to the present invention, in which the central portion of the valve is shown partially broken away;

FIG. 1B is a bottom view showing the first embodiment of the constant-rate discharge valve;

DESCRIPTION OF THE PREFERRED EMBODIMENTS

Figure 2:
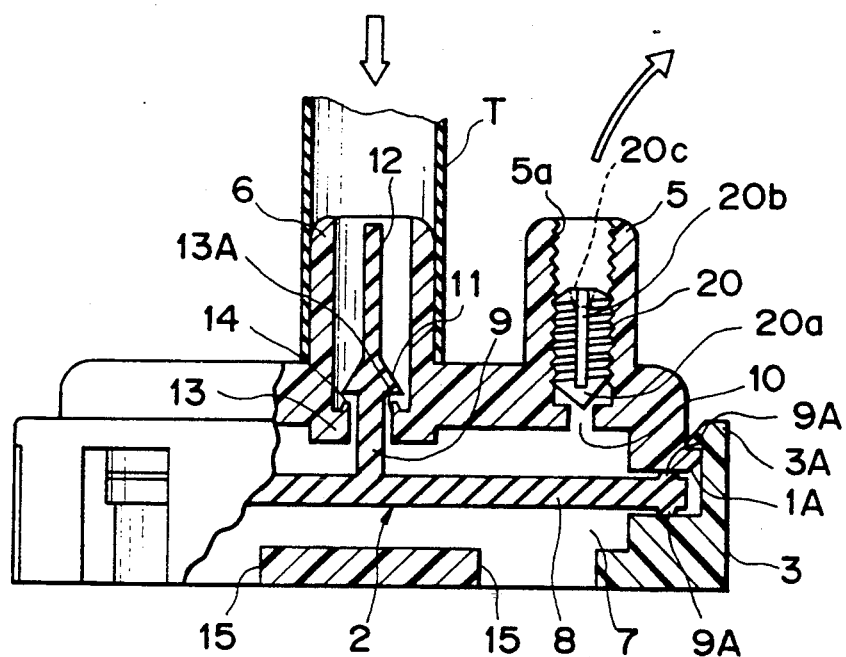
FIG. 2 is a partial sectional view illustrating a second embodiment of a constant-rate discharge valve according to the present invention, in which the central portion of the valve is shown partially broken away.

Preferred embodiments in which the constant-rate discharge valve of the present invention is applied will now be described with reference to the drawings.

With reference to FIGS. 1A and 1B, there is shown a cylindrical housing 1 the upper side of which is integrally formed to have an air inlet port 6 and an air outlet port 5 in such a manner that these ports communicate with an air chamber 4 within the housing 1. The air inlet port 6 is formed as a hollow projection in such a manner that a flexible plastic tube serving as piping, described below, may be connected thereto with ease. As will be set forth later, the valve is connected to an electronic sphygmomanometer via the flexible plastic tube.

The central portion of the housing 1 at which the outlet port 5 is provided is formed to have a control orifice 10 of the kind shown. Control of the discharge operation is performed via the control orifice 10.

A diaphragm 8 made of rubber is disposed within the housing 1 and is capable of moving up and down in the drawing of FIG. 1A so as to vary the volume of the air chamber 4. The diaphragm 8 is provided at its approximate center with a valve 11 via a rod 9. The upper portion of the valve 11 is provided with a gate body 12. A flange 13 having a flange hole 13A is formed at approximately the central portion of the housing 1. The valve 11 is capable of assuming a state (not shown) in which its lower surface seals off the upper surface of the flange 13, and a state in which its lower surface opens the upper surface of the flange 13. This latter state is that illustrated in FIG. 1A.

More specifically, with the valve 11 in the state illustrated, which is the non-actuated state, air which flows in from the inlet port 6 in the direction of the arrow in FIG. 1A passes through the gap between the lower surface of the valve 11 and the wall of the flange hole 13A, after which the air passes through the air chamber 4 and then freely through outlet port 5 to be released into the atmosphere, as indicated by the arrow.

The lower surface of the valve 11 and the wall at the mouth of the flange hole 13A are formed to be smooth so that the former will come into snug abutting contact with the latter. In order that the valve 11 will reliably contact and seal off the mouth of the flange hole 13A even under the action of a very small force, the mouth of the flange hole 13A is provided with an annular projection 14.

An annular clearance is defined between the inner wall of the flange hole 13A and the outer wall of the rod 9 connecting the diaphragm 8 to the valve 11. In order to achieve the required air flow rate without impediment, the dimensions of this clearance are obtained through calculation, described below.

The lower surface of the housing 1 along the inner circumference thereof is smoothly finished at its surface of contact with the diaphragm 8 in order to maintain the diaphragm 8 in a hermetically sealed (air light) state with the housing 1. It is also arranged so that when the valve is assembled to clamp the diaphragm 8 between the housing 1 and a back-up body or cover 3, no air will leak from the surface of contact with the diaphragm 8 (i.e., the assembly is an air tight).

Further, the housing 1 is provided over its entire outer circumference with a fitting member 1A so that when the back-up body or cover 3 is fitted onto the outer circumferential portion of the housing 1, the illustrated assembled state can be achieved even if separate, special-purpose mounting parts are not provided.

The diaphragm 8 is made of rubber or flexible plastic and is integrally molded with the valve 11, as set forth above. The entire outer circumferential portion of the diaphragm 8 preferably is provided with a projection 9A that is readily depressed to form a hermetic air tight seal at the surface of contact with the housing 1 after assembly.

The slender gate shaft 12 at the distal end of the valve 11 is the residue of a gate portion that is for injecting the raw material of rubber or the like when the valve 11 and diaphragm 8 are integrally molded. By leaving this gate portion attached, the gate shaft 12 can be pulled upward from the side of the inlet port 6 at the time of assembly when the valve 11 whose outer diameter is larger than the inner diameter of the flange hole 13A is passed through the flange hole 13A. By pulling up the gate shaft 12 in this manner, the valve 11 is forcibly fitted into the flange hole 13A. This facilitates the assembly operation.

The back-up body or cover 3 is assembled in such a manner that the diaphragm 8 is sandwiched between it and the housing 1, as described earlier. The purpose of this is to hermetically seal the air chamber 4 by pressing the diaphragm 8 against the housing 1, and to attach the diaphragm to the housing in an air-tight state. Accordingly, the surface of the back-up body or cover 3 where it contacts the diaphragm 8 is formed so that the inner diameter of the back-up body is the same as the diameter of the housing 1. The back-up body or cover 3 is provided with open holes or openings 15 in communication with the atmosphere in order that the pressure acting upon the diaphragm will be equal to atmospheric pressure.

In order to prevent the valve 11 from being forced out through the flange hole 13A owing to an excessive force which acts upon the valve 11 when the diaphragm 8 is subjected to an excessive force, the arrangement is such that the diaphragm 8 will abut against the inner surface of the back-up body or cover 3 if the diaphragm expands by more than a prescribed amount. Thus, the diaphragm 8 cannot expand excessively and the valve 11 is prevented from sustaining damage.

Fitting members 3A are provided on the outer circumferential portion of the back-up body or cover 3 at eight equally spaced locations in order that these may mate with the fitting member 1A provided on the outer circumferential portion of the housing 1. The dimensions of the fitting member 3A are such that the housing 1 and the outer circumferential portion of the back-up body or cover 3 will mate at a position where they will be in contact with the surface of the diaphragm 8 along its entire circumference to snugly compress the projection 9A on the outer circumferential portion of the diaphragm.

In general, the amount of flexure of the diaphragm is expressed numerically in the form of a disk-shaped diaphragm whose periphery is fixed. The details are also set forth in handbooks on mechanical engineering.

Letting P represent the desired pressure, d the clearance between the valve 11 and the inner wall of the flange hole 13A, t the thickness of the diaphragm 8, R the radius of the diaphragm 8 and E Young's modulus of the diaphragm 8, we have the following equation:

$$d = \frac{3(m^2 - 1)PR^4}{16Em^2t^3}$$

In the foregoing equation, 1/m is Poisson's ratio, which is approximately 0.5 for rubber; hence, m=2. If rubber having a Young's modulus of 24 kgf/cm² is used and the valve is set to operate at a pressure of 20 mmHg, then the pressure will be P=20 mmHg=0.026 kgf/cm². Therefore, if the diaphragm has a radius of 1 cm and a thickness of 0.1 cm, we have $$d = \frac{3(2^2 - 1) \times 0.026 \times 1^4}{16 \times 24 \times 2^2 \times (0.1)^3}$$

$$= \frac{0.234}{1.536} = 0.152 \text{ (cm)}$$

Thus, the dimensions of the various parts should be set in such a manner that the clearance between the valve and the wall of the flange hole will be 1.52 mm.

Rubber, besides exhibiting viscoelasticity, is such that the Young's modulus thereof varies widely with the temperature at which it is used. In addition, the precision of the operating pressure of a rubber diaphragm varies widely owing to the influence of temperature and the like. Moreover, in terms of designing a valve which operates at high pressure, diaphragm thickness is very large because the Young's modulus of rubber is exceedingly small.

Accordingly, it is permissible to superimpose a metal diaphragm on the abovementioned rubber diaphragm 8, thus constructing a valve which will operate at high pressure even with use of the rubber diaphragm 8. The metal diaphragm can be made of, e.g., stainless steel, in which case Young's modulus would be as large as $2 \times 10^7$ kgf/cm$^2$. Therefore, the operating pressure of the valve would be determined not from the elastic force of rubber but from the physical properties of a substantially metal diaphragm.

It is also permissible to cut away a portion of the metal diaphragm.

FIG. 2 illustrates another embodiment of the constant-rate discharge valve of the invention, in which portions similar to those shown in FIGS. 1A and 1B are designated by like reference characters and need not be described again. Only structural elements different from those of the embodiment of FIGS. 1A and 1B will be described. The inner circumferential surface of the outlet port 5 of the constant-rate discharge valve is formed to have threads 5a, and the control orifice 10 is shaped to have angular portions, of the kind shown, at its upper and lower parts.

A screw body 20 threadedly engaged with the threads 5a has a conical lower portion 20a, a groove portion 20b and an adjustment recess 20c. A clearance, namely a control passage, is formed between the angular portions of the control orifice 10 and the outer circumferential surface of the conical portion 20a.

In order to adjust the control passage, a screwdriver or the like is inserted into the adjustment recess 20c and the screw body 20 is turned to regulate the clearance formed between the angular portions of the control orifice 10 and the outer circumferential surface of the conical portion 20a. Air is discharged by passing through the groove 20b.

Figure 3:
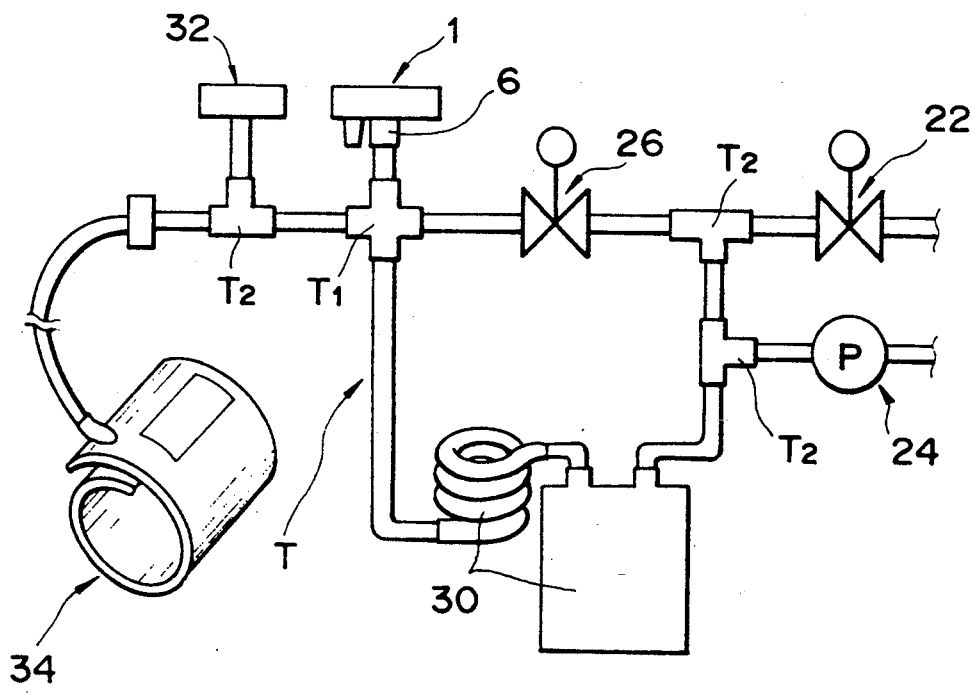
FIG. 3 is a schematic view of piping showing the pneumatic pressure system of an electronic automatic sphygmomanometer using the constant-rate discharge valve of the invention.
Figure 4A:
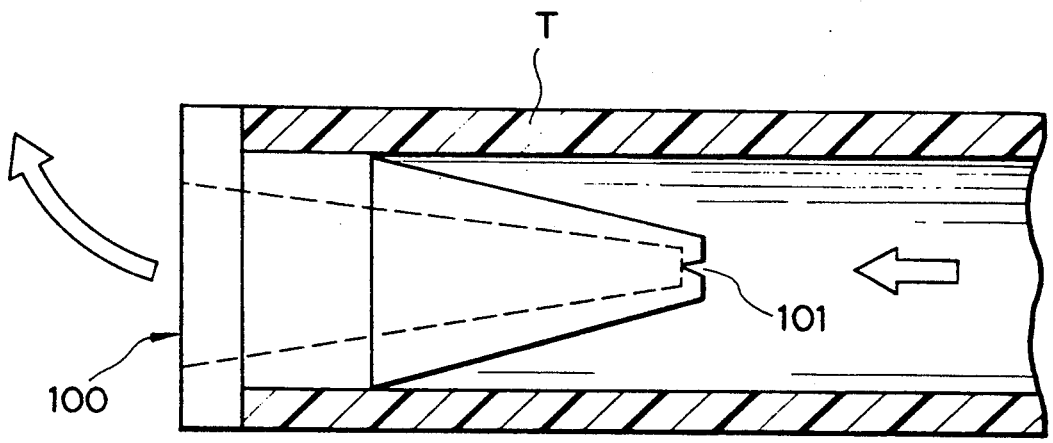
FIG. 4A is a front view showing a constant-rate discharge valve according to the prior art.
Figure 4B:
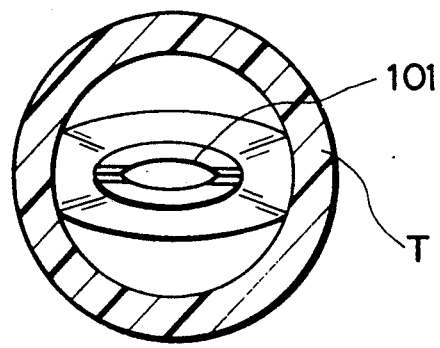
FIG. 4B is a side view of the constant-rate discharge valve according to the prior art.

FIG. 3 shows the overall piping T of an electronic automatic sphygmomanometer employing the constant-rate discharge valve 1. A cuff 34 and a motor-driven pump 24 are connected by a four-branch pipe junction T1 and a two-branch pipe junction T2. The inlet port 6 of the constant-rate discharge valve 1 is connected to the upwardly directed portion of the four-branch pipe junction T1. A pressure sensor 32 is connected via a two-branch pipe junction T2 to the leftwardly directed portion of the four-branch pipe junction T1, and the cuff 34 is connected to the leftwardly directed portion of this two-branch pipe junction T2.

The outlet port of a filter device 30 comprising a fluidic resistor and a fluid buffer bag is connected to the downwardly directed portion of the four-branch pipe junction T1. The motor-driven pump 24 is connected to the inlet port of the filter device 30 via a two-branch pipe junction T2. Connected to the upwardly directed portion of this pipe junction T2 via another two-branch pipe junction T2 are a bypass valve 26 having an electromagnetically driven solenoid, and a discharge valve 22 similarly having an electromagnetically driven solenoid.

When the pressure within the cuff 34 is less than 20 mmHg in this electronic automatic sphygmomanometer thus connected, air from the motor-driven pump 24 is caused to flow directly into the cuff 34 to inflate and deflate the cuff efficiently in a short period of time. Specifically, when cuff pressure is less than 20 mmHg, the bypass valve 26 is in the open state to allow passage of the air therethrough. As a result, the air flows directed from the pump 24 to the interior of the cuff 34.

When the cuff pressure rises to a value greater than 20 mmHg, on the other hand, the bypass valve 26 is closed to prevent air from passing through it. As a result, the air passes through the filter device 30 interposed in the pneumatic line extending from the motor-driven pump 24 to the cuff 34. The filter device 30, which comprises the abovementioned filtering elements such as the fluidic resistance element, functions as a rectifying circuit. As a result, the cuff 34 is supplied with air at a constant rate without any pulsation in cuff pressure when blood pressure is measured.

In addition, air discharge at a constant rate is performed gradually from the constant-rate discharge valve 1 also when the cuff is inflated. Since the amount of air supplied by the motor-driven pump 24 is much larger than the amount of air discharged from the constant-rate discharge valve 1, the discharge of air from the constant-rate discharge valve 1 has almost no effect upon the rate of pressurization.

Next, when the cuff is deflated, the motor-driven pump 24 is stopped and the air in the cuff 34 is gradually deflated via the constant-rate discharge valve 1. In this case, the air discharged flows in from the inlet port 6, through the air chamber 4 and then the orifice 10 and is discharged into the atmosphere from the outlet port 5. At such time, a pressure difference is produced between the air chamber 4 upstream of the orifice 10 and the atmospheric pressure side downstream of the orifice 10.

It is evident from hydraulic engineering that the pressure difference produced is proportional to the square of the flow rate of the fluid flowing through the orifice. Owing to the pressure difference, the pressure in the air chamber 4 rises, and therefore the diaphragm 8 begins to move the valve 11 in the closing direction, when the pressure difference is large, namely when the air flow rate is high. When this occurs, the amount of air which flows into the air chamber 4 from the inlet port 6 gradually decreases, and so does the amount of air discharged into the atmosphere through the orifice 10. Accordingly, the pressure difference across the orifice 10 also diminishes. As a result, the pressure in the air chamber 4 decreases and the action of the diaphragm 8 attempting to close the valve 11 is suppressed.

Conversely, when the pressure difference across the orifice 10 diminishes, namely when the air flow rate decreases, the pressure in the air chamber 4 declines and the diaphragm 8 begins to move the valve 11 in the opening direction. When this occurs, the air flowing into the air chamber 4 from the inlet port 6 grows larger and so does the amount of air discharged into the atmosphere through the orifice 10. As a result, the pressure difference produced across the orifice 10 also increases and the pressure in the air chamber 4 rises, whereby the action of the diaphragm 8 attempting to open the valve 11 is suppressed.

As described above, the constant-rate discharge valve 1 operates at all times so as to render constant the pressure difference across the orifice 10. Achieving a constant pressure difference across the orifice in this manner means achieving a constant flow rate of the fluid flowing through the valve.

Blood pressure is measured while air is discharged from the valve at a constant rate. When measurement of diastolic blood pressure ends, the discharge valve 22 and bypass valve 26 attain an open state, and the air in the cuff 34 is rapidly discharged through the bypass valve 26 and discharge valve 22, whereupon one measurement cycle is terminated.

The constant-rate discharge valve 1 utilizes the pressure difference across the orifice 10 to operate the diaphragm 8 and therefore control the opening and closing of the valve. Consequently, the constant-rate discharge valve 1 is no longer capable of operating when cuff pressure falls below the operating pressure of the diaphragm 8, namely a pressure of, e.g., 20 mmHg. However, since diastolic blood pressure never drops below 20 mmHg, the constant-rate discharge valve 1 can be used effectively in a sphygmomanometer.

It goes without saying that the means for adjusting the flow rate of the constant-rate discharge valve is not limited to the screw body mentioned above.

Thus, in accordance with the present invention as described above, there can be provided a constant-rate discharge valve which does not require troublesome operation and is capable of maintaining a constant discharge state without variance, as well as a fully automatic sphygmomanometer employing this constant-rate discharge valve.

It is also possible to provide a constant-rate discharge valve in which discharge flow rate can be adjusted, as well as an electronic sphygmomanometer which employs this constant-rate discharge valve.

As many apparently widely different embodiments of the present invention can be made without departing from the spirit and scope thereof, it is to be understood that the invention is not limited to the specific embodiments thereof except as defined in the appended claims.

What is claimed is:

1. A constant-rate discharge valve for a sphygmomanometer, for providing a constant discharge rate, comprising:
    a housing having an internal air chamber and an opening which is open to ambient atmosphere;
    first and second air passageways which are separate from said opening, each having one end open to said air chamber and communication with each other via said air chamber, said second air passageway having a control orifice for controlling an air flow rate of air flowing therethrough; and
    a valve body made of rubber-like material disposed in said housing and arranged as a partition member to permanently separate said air chamber from said opening, said valve body including a deflecting portion which deflects and causes said valve body to interrupt communication between said first and second air passageways responsive to pressure in said air chamber being greater than a predetermined pressure, and said deflecting portion staying substantially in its original shape and said valve body permitting communication between said first and second air passageways when the pressure in said air chamber is less than said predetermined pressure, said deflecting portion always being in gaseous communication with ambient atmosphere through said opening;
    said second air passageway being arranged to discharge air flowing therethrough to the atmosphere, whereby air which has flown into said valve from said first air passageway passes through said air chamber and through said control orifice and is discharged into the atmosphere from said second air passageway;
    said valve body being actuated by a pressure difference across upstream and downstream sides of said control orifice produced by the flow rate of the entrant air so as to deflect said deflecting portion and close and interrupt said communication between said first and second air passageways responsive to said pressure difference being above a predetermined pressure difference, and said valve body being substantially in it original shape when said pressure difference is below said predetermine pressure difference such that said valve body permits communication between said first and second air passageways, whereby the flow rate of air discharged from said second air passageway via said control orifice is rendered constant.

2. The constant-rate discharge valve of claim 1 wherein said control orifice includes adjusting means for adjusting a discharge flow rate therethrough.

3. The constant-rate discharge valve of claim 2, wherein said adjusting means comprises a turnable screw body having a threaded outer circumferential surface threadedly engaged with a female screw portion formed on an inner surface of said second air passageway, said screw body being turnable in said second air passageway to directly adjust an opening area of said control orifice.

4. The constant-rate discharge valve of claim 1, wherein:
    said housing comprises a first housing portion which has said internal air chamber therein and which includes said first air passageway and said second air passageway, and a valve cover snap fitted onto said first housing portion and having said open hole therein; and
    said valve body is disposed between said first housing portion and said valve cover in an air tight relationship between said first housing portion and said valve cover where they contact said valve body, so that said valve body makes an air tight separation between said air chamber and said opening.

5. The constant-rate discharge valve of claim 1, wherein said valve body comprises:
    a diaphragm portion which perform a predetermined flexing movement operation responsive to said pressure difference;
    a movable valve portion coupled to said diaphragm portion and which opens and closes said first air passageway responsive to said flexing movement of said diaphragm portion; and
    a gate portion which is integrally formed with said valve portion and being pulled up through said first air passageway, thus facilitating assembly.

6. The electronic automatic sphygmomanometer of claim 1, wherein said opening is positioned on one sided of said deflecting portion of said valve body and said first and second passageways are positioned on an opposite side of said deflecting portion of said valve body.

7. An electronic automatic sphygmomanometer comprising:

a cuff;

air feeding means for feeding air into said cuff; and a constant-rate discharge valve connected between said cuff and said air feeding means;

said constant-rate discharge valve including:

a housing having an internal air chamber and an opening which is open to ambient atmosphere;

first and second air passageways which are separate from said opening, each having one end open to said air chamber and communication with each other via said air chamber, said second air passageway having a control orifice for controlling the flow rate of air flowing therethrough; and a valve body disposed in said housing and arranged as a partition member to permanently separate said air chamber from said opening, said valve body comprising means including a deflecting portion for interrupting air communication between said first and second air passageways when pressure in said air chamber is greater than a predetermined pressure and for permitting air communication between said first and second air passageways when said pressure in said air chamber is less than said predetermined pressure, said deflecting portion always being in gaseous communication with ambient atmosphere through said opening.

8. The electronic automatic sphygmomanometer of claim 7, further comprising by-pass valve means and a filter device which are connected in parallel between said cuff and said air feeding means.

* * * * *

UNITED STATES PATENT AND TRADEMARK OFFICE
CERTIFICATE OF CORRECTION

PATENT NO. : 5,143,077
DATED : September 1, 1992
INVENTOR(S) : KOBAYASHI, Susumu It is certified that error appears in the above-identified patent and that said Letters Patent is hereby corrected as shown below:

Column 9, line 2 (claim 6), replace "sided" with --side--.

Column 9, line 19 (claim 7), replace "communication" with

-communicating--.

Signed and Sealed this

Twenty-eighth Day of September, 1993

*Attest:*

BRUCE LEHMAN

*Attesting Officer*     *Commissioner of Patents and Trademarks*